United States Patent [19]
Becker et al.

[11] Patent Number: 5,698,206
[45] Date of Patent: Dec. 16, 1997

[54] TOPICAL COMPOSITION FOR THE TREATMENT OF SPIDER VEINS

[75] Inventors: Philip E. Becker, Jupiter; Mary Lou Doepker, Miami, both of Fla.

[73] Assignee: Swedish Herbal Systems, Inc., Jupiter, Fla.

[21] Appl. No.: 760,981

[22] Filed: Dec. 5, 1996

[51] Int. Cl.⁶ .................................................. A61K 7/00
[52] U.S. Cl. ................ 424/401; 424/63; 424/64; 424/66; 424/195.2
[58] Field of Search ..................... 424/63, 64, 66, 424/401, 195.1

[56] References Cited

U.S. PATENT DOCUMENTS

| | | | |
|---|---|---|---|
| 4,883,659 | 11/1989 | Goodman | 424/78.03 |
| 4,906,461 | 3/1990 | Chambers | 424/74 |
| 5,039,516 | 8/1991 | Goodman | 424/59 |
| 5,266,318 | 11/1993 | Taylor-McCord | 424/195.1 |

*Primary Examiner*—Thurman K. Page
*Assistant Examiner*—D. Faulkner
*Attorney, Agent, or Firm*—McHale & Slavin, P.A.

[57] ABSTRACT

A composition for topical application to the skin having an effective amount of natural herbs placed in a carrier oil for use in combination with an individual having ingested a moderate amount of Vitamin C. The composition provides for treatment of surface vein disorders, namely spider and varicose veins, by rejuvenating the veins and associated vein valves providing normal blood transfer.

4 Claims, No Drawings

TOPICAL COMPOSITION FOR THE TREATMENT OF SPIDER VEINS

FIELD OF THE INVENTION

This invention relates to the treatment of vein disorders, and more particularly to a topically applied lotion for the treatment of spider veins.

BACKGROUND

Varicose and spider veins are terms used to describe two problematic vein disorders. The veins appear in the legs, particularly around the ankles, calves, thighs and inside the knees. The disorder is a result of blood collecting in the veins which results in swelling. In many instances the blood flows backwards, a condition that may cause the vein to further expand, causing an unsightly situation.

There are two principal vein types in the legs. Deep veins carry about 90 percent of the blood, the remainder carried in veins which are often visible just under the skin. Once circulating blood has oxygenated tissues, the blood is collected by the veins and pumped to veins in the abdomen, which returns the blood to the heart. Valves prevent blood from draining back down the leg under the force of gravity. As the vein must support a column of blood, if the valve fails a pooling of blood occurs. This is most noticeable in superficial veins which become swollen and distorted. If the backflow of blood is severe or prolonged, the tissues may lack nourishment causing the skin to become thin, hard, dry, scaly, and discolored.

The medical field does not have a definitive reason as to the cause of such conditions, which is predominantly found in women, other than a belief that the condition is a result of excessive pressure within the vein. The condition is aggravated by athletic movement, heat, pregnancy, excessive time standing, and obesity. In many instances the cause is believed to be hereditary.

Sclerotherapy is a known treatment wherein a saline solution is injected into the damaged vein. The solution is an irritant causing the vein to collapse. The collapse of the vein causes its work to be taken over by other veins, causing the damaged vein to disappear. The treatment requires that each vein damaged is injected with the solution which may lead to bruising of the treated area, and possibly an allergic reaction. In addition, the procedure does not eliminate the problem as the blood is directed to another vein which may also collapse. There are no maintenance-type injections, treatment is directed as each vein appears. Treatment can also be expensive, requires administration by a trained medical professional, and includes the inherent risks of needle injection, as well as the inconvenience of multiple visits to a medical facility.

Photoderm VL and Sclerolaser are a laser-like process utilizing a pulsed light directed at the damaged vein. The laser uses a specific wavelength and duration to treat veins by vaporizing the vein with a beam of light. This treatment may cause temporary swelling and discolorization of the damaged area and must be administered by a trained individual. The treatment requires multiple sessions to address each vein and the possibility exists the veins that take over the load may also fail.

Topically applied compositions also exist relating to the treatment of skin disorders. U.S. Pat. No. 5,510,391 discloses a composition for the treatment of blood vessel disorders such as vascular problems by use of a composition of vitamin K and alcohol, both ethyl and isopropyl. U.S. Pat. No. 5,116,617 is directed to the topical use of Defibrotide for treatment of blood capillary vessels. Relevant compositions not directly related to the treatment of veins include: U.S. Pat. No. 5,104,657 directed to the topical application of chloramphenicol, gentamicin and nystatin for skin disorders. U.S. Pat. No. 4,722,843 discloses a moisturizing nutritive and healing skin cream containing avocado and cucumber juice. U.S. Pat. No. 4,331,653 discloses a composition for treating skin disorders having polyethylene glycol stearate and an acidic metallic salt. U.S. Pat. No. 4,282,250 discloses ointment for treatment of skin disorders and in particular a carboxylic acid for treatment of indolent leg ulcer.

U.S. Pat. No. 5,520,919 discloses a Vitamin A palmitate for rejuvenating of skin. U.S. Pat. No. 5,425,954 discloses a topically applied amino acid with a vitamin complex composition for treatment of various skin conditions. U.S. Pat. No. 4,005,191 discloses a topical ointment composition having calcium carbonate, magnesium hydroxide, and aluminum hydroxide such as inflammation. U.S. Pat. No. 5,350,774 discloses a topical composition consisting of myrrh, hamamelis and chamomile for treatment of skin disorders.

Thus, what is lacking in the art is a safe and effective means of treating spider veins, with an all natural topical application.

SUMMARY OF THE INVENTION

The instant invention is a composition of herbs placed in a lotion for treatment of vein disorders. The composition is based upon a percentage of ingredients that is all natural, and capable of penetrating the epidermis of the skin for strengthening the walls of the affected veins. The treatment is enhanced when the composition is taken in conjunction with a quantity of vitamin C and water. The vitamin C is taken orally and operates to remove oxidants from the blood, the water helps to flush the body of impurities.

The composition is topically applied to the skin of a human in the form of a lotion, cream, gel, or ointment containing an effective amount of Sea Kelp, Algae Extract, Panthenol, Jojoba Oil, Calendula Oil, Marigold Extract, Chickweed Extract, Lactic Acid, Carrot Oil, Niacin, Vitamin E, White Willow Extract, Arnica Extract, Horse Chestnut Extract, and Red Clover Extract, placed in a carrier oil. The composition is applied sparingly over the affected area twice a day. The lotion is softly worked into the skin allowing penetration of the epidermis.

Thus, an objective of the invention is to disclose a safe and effective natural treatment for vein disorders in the legs and in particular, spider veins.

The composition of herbs provides a rejuvenation of surface veins for restoring blood transfer.

Still another objective is to provide a composition for treatment of surface veins that is enhanced when used in combination with vitamin C, the vitamin C taken internally.

Yet still another objective is to have a topically applied lotion that allows for maintenance of the legs to inhibit the creation and/or return of spider veins.

Other objectives and advantages of this invention will become apparent from the following description wherein are set forth, by way of illustration and example, certain embodiments of this invention.

DETAILED DESCRIPTION OF THE PREFERRED EMBODIMENT

Although the invention will be described in terms of a specific embodiment, it will be readily apparent to those skilled in this art that various modifications, rearrangements and substitutions can be made without departing from the spirit of the invention. The scope of the invention is defined by the claims appended hereto.

The present composition provides an effective amount of natural herbs placed in a carrier emulsion for treatment of spider veins and associated vein disorders. The composition is applied twice daily to the skin by rubbing a small amount of the concentrated composition into the skin. The effect of the composition is to strengthen the walls of the veins restoring the flow of blood. It has been found that the vein valves are also strengthened.

The composition is used in conjunction with carrier oils and water to form a lotion allowing the composition to be absorbed into the skin. The preferred embodiment, based upon a percent of volume, is as follows:

| Embodiment No. 1 | |
|---|---|
| Ingredient | Percent of Volume |
| Water | 63.80 |
| Mineral Oil | 4.00 |
| Sesame Oil | 2.50 |
| Sea Kelp | .80 |
| Soybean Oil | 4.40 |
| Algae Extract | 1.90 |
| Stearic Acid | 3.00 |
| Glyceryl Stearate & PEG 100 | 5.00 |
| Cetyl Alcohol | .50 |
| Panthenol | .05 |
| Jojoba Oil | .30 |
| Germaren II | .50 |
| Triethanolamine | .50 |
| Calendula Oil | .20 |
| Marigold Extract | .60 |
| Chickweed Extract | .80 |
| Lactic Acid | 2.50 |
| Carrot Oil | .02 |
| Niacin | .02 |
| Propylene Glycol | 5.00 |
| Vitamin E | .01 |
| White Willow Extract | .80 |
| Arnica Extract | .80 |
| Horse Chestnut Extract | .80 |
| Red Clover Extract | .80 |
| Glydant/Hydanthion | .40 |

All percentages and ratios are by weight of the total composition and made at 25 degrees C.

The active ingredients and their range of equivalents are: Sea Kelp 0.1–8.0; Algae Extract 0.1–5.0; Panthenol 0.05–1.0; Jojoba Oil 0.1–3.0; Calendula Oil 0.1–0.75; Marigold Extract 0.1–2.0; Chickweed Extract 0.1–2.0; Lactic Acid 0.5–4.0; Carrot Oil 0.01–0.1; Niacin 0.01–0.5; Vitamin E 0.01–0.5; White Willow Extract 0.1–2.0; Arnica 0.01–2.0; Horse Chestnut Extract 0.01–1.0; Red Clover Extract 0.01–2.0.

The preferred carrier oil is a combination having a range of volumes acceptable for use, based upon a percent of volume; Mineral Oil 0.1–8.0; Sesame Oil 0.1–8.0; Soybean Oil 0.1–8.0; Jojoba Oil 0.1–3.0; Calendula Oil 0.1–0.75; Carrot Oil 0.01–0.1.

EXAMPLE 1

A topical composition is prepared according to Embodiment No. 1 forming a lotion, the fluidity of which is dependant upon the amount of water added. The composition is gently rubbed into the skin and within four weeks begins to generate the desired results. The results initially reduce the size and coloration of the spider veins. Continuation of the lotion in a reduced amount provides maintenance by helping to further reduce spider veins as well as inhibit the causation of new veins.

The water acts as a vehicle to enable the concentration to form a lotion suitable for convenient topical application to the skin. Vehicles other than water can include liquid or solid emollients, solvents and powders found in cosmetic formulations. Emollients added to the water act as a carrier to achieve unrestricted topical application.

EXAMPLE 2

A topical composition is prepared according to Embodiment No. 1 forming a lotion, the fluidity of which dependant upon the amount of water added. The individual ingests a moderate amount of Vitamin C, the recommended amount being 3,000 mg together with at least six 8 ounce glasses of water consumed during a day. The composition is gently rubbed into the skin and within four weeks begins to generate the desired results. The results initially reduce the size and coloration of the spider veins. Continuation of the lotion in a reduced amount provides maintenance by helping to further reduce spider veins as well as inhibit the causation of new veins. Vitamin C operates to remove oxidants from the blood, the water helps to flush the body of impurities.

The composition can also be applied before exposure to direct sunlight as the composition provides a natural sunscreen. The moisturizing properties further permit employment directly after a shower or upon leaving of a swimming pool. Natural side effects in some people are beneficial and relate to the reduction of the throbbing of varicose veins, age and liver spots, as well as accelerated healing of bruises.

It is to be understood that while we have illustrated and described certain forms of our invention, it is not to be limited to the specific forms or arrangement herein described and shown. It will be apparent to those skilled in the art that various changes may be made without departing from the scope of the invention.

What is claimed is:

1. A treatment for spider and varicose vein disorders comprising a composition topically applied to the skin of a human, said composition being in the form of a lotion, cream, gel, or ointment containing an effective amount of Sea Kelp, Algae Extract, Panthenol, Jojoba Oil, Calendula Oil, Marigold Extract, Chickweed Extract, Lactic Acid, Carrot Oil, Niacin, Vitamin E, White Willow Extract, Arnica Extract, Horse Chestnut Extract, Red Clover Extract, placed in a carrier oil and used in combination with a patient ingesting a moderate amount of Vitamin C.

2. The composition according to claim 1 wherein said carrier oil is a mixture of mineral oil, sesame oil, soybean oil, jojoba oil and calendula oil.

3. The composition according to claim 1 wherein said active ingredients form a percent of volume comprising: Sea Kelp 0.1–8.0; Algae Extract 0.1–5.0; Panthenol 0.05–1.0; Jojoba Oil 0.1–3.0; Calendula Oil 0.1–0.75; Marigold Extract 0.1–2.0; Chickweed Extract 0.1–2.0; Lactic Acid 0.5–4.0 Carrot Oil 0.01–0.1; Niacin 0.01–0.5; Vitamin E 0.01–0.5; White Willow Extract 0.1–2.0; Arnica 0.01–2.0; Horse Chestnut Extract 0.01–1.0; Red Clover Extract 0.01–2.0.

4. A composition for topical application to the skin for the treatment of surface vein disorders wherein the surface vein disorders are spider and varicose veins comprising as a percent of volume:

| | |
|---|---|
| Mineral Oil | 4.00 |
| Sesame Oil | 2.50 |
| Sea Kelp | .80 |
| Soybean Oil | 4.40 |
| Algae Extract | 1.90 |
| Stearic Acid | 3.00 |
| Glyceryl Stearate & PEG 100 | 5.00 |
| Cetyl Alcohol | .50 |
| Panthenol | .05 |
| Jojoba Oil | .30 |
| Germaren II | .50 |
| Triethanolamine | .50 |
| Calendula Oil | .20 |
| Marigold Extract | .60 |
| Chickweed Extract | .80 |
| Lactic Acid | 2.50 |
| Carrot Oil | .02 |
| Niacin | .02 |
| Propylene Glycol | 5.00 |
| Vitamin E | .01 |
| White Willow Extract | .80 |
| Arnica Extract | .80 |
| Horse Chestnut Extract | .80 |
| Red Clover Extract | .80 |
| Glydant/Hydanthion | .40 | admixed to water having a 63.80 percent of volume.

\* \* \* \* \*